United States Patent [19]

Luo

[11] 4,440,566

[45] Apr. 3, 1984

[54] HERBICIDAL SUBSTITUTED 2-(1-(OXYAMINO)-ALKYLIDENE)-CYCLOHEXANE-1,3-DIONES

[75] Inventor: Tatao Luo, El Sobrante, Calif.

[73] Assignee: Chevron Research Company, San Francisco, Calif.

[21] Appl. No.: 406,423

[22] Filed: Aug. 9, 1982

Related U.S. Application Data

[63] Continuation-in-part of Ser. No. 405,228, Aug. 5, 1982, abandoned, which is a continuation of Ser. No. 210,206, Nov. 25, 1980, abandoned.

[51] Int. Cl.$^3$ .................... C07C 131/00; A01N 31/06; A01N 33/24
[52] U.S. Cl. .......................................... 71/98; 71/106; 71/107; 71/121; 560/10; 560/35; 560/18; 560/100; 560/106; 560/107; 560/125; 560/250; 564/256
[58] Field of Search .................... 564/256; 560/10, 18, 560/35, 100, 106, 107, 125, 250; 71/98, 106, 107, 121

[56] References Cited

U.S. PATENT DOCUMENTS

| | | | |
|---|---|---|---|
| 3,943,176 | 3/1976 | Dunbar et al. | 71/98 |
| 3,950,420 | 4/1976 | Sawaki et al. | 560/125 |
| 3,989,737 | 11/1976 | Sawaki et al. | 564/256 |
| 4,011,256 | 3/1977 | Sawaki et al. | 560/125 |
| 4,033,754 | 7/1977 | Sawaki et al. | 560/125 |
| 4,249,937 | 2/1981 | Iwataki et al. | 71/98 |

FOREIGN PATENT DOCUMENTS 46860 3/1983 European Pat. Off. .

*Primary Examiner*—Natalie Trousof
*Assistant Examiner*—L. Hendriksen
*Attorney, Agent, or Firm*—D. A. Newell; T. G. De Jonghe; L. S. Squires

[57] ABSTRACT

Substituted 2-[1-(oxyamino)alkylidene]-cyclohexane-1,3-diones have herbicidal activity against grassy weeds.

24 Claims, No Drawings

HERBICIDAL SUBSTITUTED 2-(1-(OXYAMINO)-ALKYLIDENE)-CYCLOHEXANE-1,3-DIONES

CROSS REFERENCE TO RELATED APPLICATIONS

This application is a continuation-in-part of U.S. Ser. No. 405,228, filed on Aug. 5, 1982, now abandoned, which is a continuation of U.S. application Ser. No. 210,206, filed Nov. 25, 1980 and now abandoned.

BACKGROUND OF THE INVENTION

U.S. Pat. No. 4,011,256 discloses herbicidal cyclohexane-1,3-diones.

SUMMARY OF THE INVENTION

This invention relates to novel herbicidal compounds, compositions and methods of use thereof. It has been found that novel haloalkyl, haloalkenyl and haloaryl-substituted 2-[1-(oxyamino)-alkylidene]-cyclohexane-1,3-diones are particularly useful as grassy herbicides in both pre- and post-emergent applications.

DESCRIPTION OF THE INVENTION

The compounds of the invention have the structural formula (I):

wherein R is alkyl of 1 to 6 carbon atoms or phenyl;

$R^1$ is haloalkyl of 1 to 6 carbon atoms, haloalkenyl of 2 to 6 carbon atoms, haloaryl of 6 to 10 carbon atoms, halobenzyl, all of which contain 1 to 3 halogen atoms; cycloalkyl of 5 to 7 carbon atoms or benzyl substituted with 1 to 3 alkyl groups of 1 to 4 carbon atoms or haloalkyl groups of 1 to 4 carbon atoms and 1 to 9 halogen atoms;

$R^2$ and $R^3$ are independently hydrogen, alkyl of 1 to 3 carbon atoms, alkylthio of 1 to 6 carbon atoms, or alkylthioalkyl of 2 to 8 carbon atoms;

$R^4$ is hydrogen, or carbalkoxy of 2 to 4 carbon atoms;

$R^5$ is hydrogen, a cation, or $$-\overset{O}{\underset{\|}{C}}R^6$$

wherein $R^6$ is alkyl of 1 to 6 carbon atoms or aryl of 6 to 10 carbon atoms.

A particularly preferred class of compounds within the scope of the invention are substituted 2-[1-(oxyamino)-alkylidene]-5,5-dialkylcyclohexane-1,3-diones.

Representative R groups are methyl, ethyl, n-propyl, isopropyl, n-butyl, isopentyl, neopentyl, n-hexyl and phenyl.

Preferably R is alkyl of 1 to 6 carbon atoms. Most preferably R is alkyl of 1 to 3 carbon atoms. Most preferably R is ethyl or propyl.

Representative $R^1$ groups are chloromethyl, bromomethyl, fluoromethyl, 2-chloroethyl, 2-bromoethyl, 3,4-dichlorobutyl, 6-chlorohexyl, 3-cis-chloroallyl, 2,3-cis-dichloroallyl, 2-chloroallyl, 4,4-dichloro-but-3-enyl, 4-bromo-3-bromomethyl-but-2-enyl, 5,5-dibromo-4-methyl-pent-2-enyl, 2,5-dichloro-hex-3-enyl, p-fluorophenyl, p-fluorobenzyl, p-chlorobenzyl, p-bromophenyl, p-bromobenzyl, 3,4-dichlorophenyl, 3,4-dichlorobenzyl, 2-fluorophenyl, 2-fluorobenzyl, 2,4,6-trichlorophenyl, 2,4,6-trichlorobenzyl, 1-bromo-naphth-2-yl, 2-chloro-naphth-1-yl, cyclopentyl, cyclohexyl, cycloheptyl, p-methylbenzyl, m-methylbenzyl, 2,4,6-triethylbenzyl, p-butylbenzyl, p-isopropylbenzyl, and p-trifluoromethylbenzyl.

Preferably $R^1$ is haloalkenyl of 2 to 6 carbon atoms and 1 to 3 halogen atoms or halobenzyl of 1 to 3 halogen atoms. Most preferably $R^1$ is haloallyl, especially, 3-trans-chloroallyl or monohalobenzyl, especially 4-chlorobenzyl.

Representative $R^2$ and $R^3$ groups are hydrogen, methyl, ethyl, propyl, methylthio, ethylthio, n-butylthio, methylthiomethyl, ethylthiomethyl, propylthiopropyl, ethylthiohexyl.

Preferably $R^2$ and $R^3$ are alkyl of 1 to 3 carbon atoms or one of $R^2$ or $R^3$ is hydrogen and the other is alkylthioalkyl. Most preferably $R^2$ and $R^3$ are both methyl or one of $R^2$ or $R^3$ is hydrogen and the other is 2-ethylthiopropyl.

Representative $R^4$ groups are hydrogen, carbomethoxy, carboethoxy, carbopropoxy. Preferably $R^4$ is hydrogen.

Representative $R^5$ groups are hydrogen, $NH_4+$, $Na+$, $K+$, $Ca++$, acetyl, propionyl, butyryl, isobutyryl, isovaleryl, 3,3-dimethylbutyryl, benzoyl, 1-naphthoyl, 2-naphthoyl. Preferably $R^5$ is hydrogen.

The compounds of my invention may be prepared according to the following scheme:

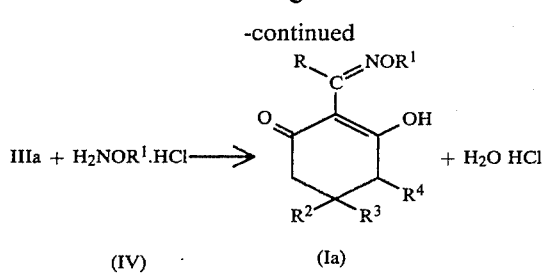

The appropriate intermediates of the formula (IV) may be made according to the following reaction sequence:

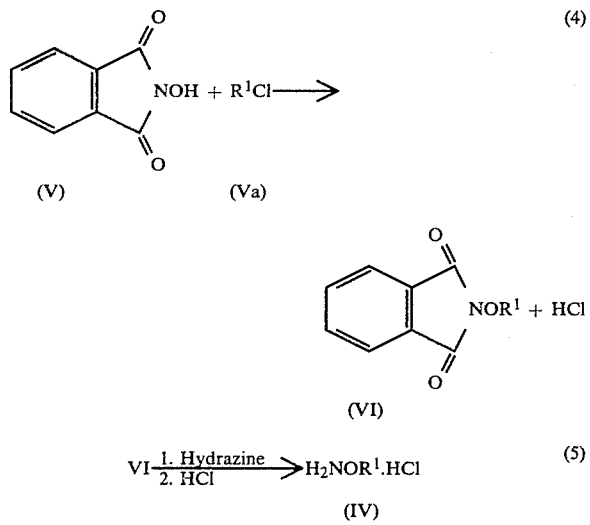

Compounds of the formula (I) wherein $R^5$ is other than hydrogen may be prepared according to conventional procedures by treating the hydroxy compound (Ia) with an appropriate basic salt to yield compounds wherein $R^5$ is $Na^+$, $NH_4^+$, $Ca^{++}$, etc. Similarly, the hydroxy compound (Ia) may be acylated by treatment with an appropriate acid halide to yield compounds wherein $R^5$ is

Reaction (1) above may be performed at ambient temperature employing substantially equimolar amounts of the dione (II) and acid halide (IIa). Preferably the acid chloride (X=Cl) is used. The reaction may be conducted in an organic solvent, such as, halogenated hydrocarbons, ethers or glycols. It is preferred that a base be present, such as an organic amine or alkali metal carbonate salt, in order to quench the hydrogen halide which is evolved. Preferred organic amines are pyridine and trialkylamines such as triethylamine. Pressure conditions are not critical and atmospheric pressure may be conveniently employed.

Reaction (2) may be performed in an inert organic solvent, such as, halogenated hydrocarbons or ethers. At least two moles of aluminum chloride per mole of ester (III) is used. Upon work-up, the crude product must be quenched with a proton-donor, preferably a mineral acid such as hydrochloric acid, to produce the trione (IIIa).

Reaction (3) is a conventional oxime forming condensation. Since the hydrochloride salt (IV) is employed, it is first neutralized with a base, preferably an alkali metal alkoxide, before combining with the trione (IIIa) or the tree base from Reaction 5 can be used directly. The reaction may be performed in an inert organic solvent, preferably lower alcohols.

Reaction (4) is a conventional alkylation and may be performed in inert organic solvents such as dimethylsulfoxide, acetonitrile, ethers, glycol ethers or hydrocarbons. The reaction is performed in presence of a base, such as potassium carbonate at ambient temperature.

Reaction (5) may be performed at elevated temperatures, preferably 30°-100° C. The phthalimide (VI) is preferably heated at atmospheric pressure with slight molar excess of hydrazine in an inert organic solvent, such as a lower alcohol, to reflux temperature. The crude mixture is then cooled and optionally quenched with a mineral acid, preferably hydrochloric acid, yielding the product salt (IV) or the tree base can be used directly in Reaction 3.

As an alternative to reactions (1) and (2) above the trione (IIIa) may be formed in one step by treating the dione (II) with the acid halide (IIa) in a halogenated hydrocarbon solvent, preferably carbon tetrachloride, in the presence of trifluoromethyl sulfonic acid. Typically, the reaction is performed at elevated temperature (30°-150° C.) and is complete within 90 hours but yields a mixture of products. Since the combined reaction time of reactions (1) and (2) is about 24 hours, and results in a purer product, the two-step sequence of reactions (1) and (2) is preferred to the one-step alternative.

The starting materials of Formula II can be prepared by known procedures or obvious modification thereof (e.g. substitution of appropriate starting material). The compunds of Formula II can be conveniently prepared by the following process schematically represented by the following overall reaction equations

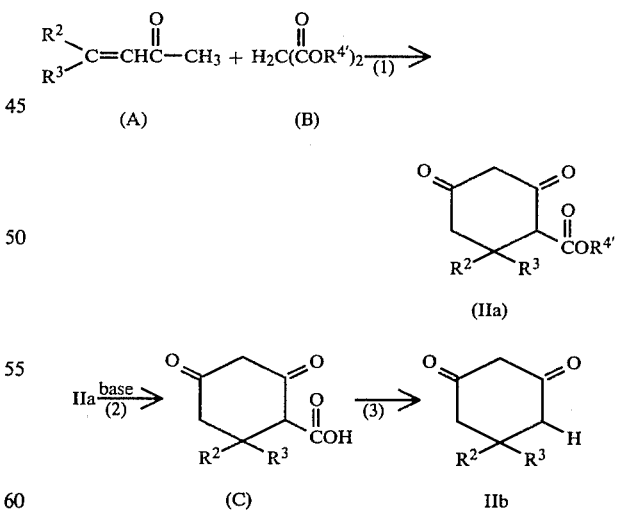

wherein $R^{4'}$ is alkyl of 1 through 3 carbon atoms and $R^2$ and $R^3$ are as defined hereinabove.

These reactions are conventional type reactions and can be conducted in the usual manner. The first reaction step is typically conducted by contacting compound A with compound B and a base (e.g. alkali metal alkoxides) under reactive conditions preferably in an inert solvent (e.g. alkanol, e.g. ethanol). Typically, the reaction is conducted at about from 60° to 110° C. using about from 0.5 to 1.5 moles, preferably 0.9 to 1.1 moles, of compound A and of the base per mole of compound B.

In the second step the ester moiety of compound IIa is base hydrolyzed to the carboxylic acid, for example, by contacting metallic sodium in alkanol (e.g. ethanol) or alkali metal hydrogen at temperatures in the range of from about 60° to 110° C. By combining the reactants Steps 1 and 2 can be conducted together.

In the third step, compound C can be decarboxylated via treatment with a strong inorganic acid (e.g. hydrochloric acid, sulfuric acid). This step is typically conducted at temperatures in the range of 25° to 110° C. and can be conveniently conducted in situ after completion of the base hydrolyzation, Step 2.

The compounds of Formula IIIa can also be prepared by reacting the compounds of Formula II with the corresponding anhydride in the presence of an organic base, preferably in an excess of anhydride or inert organic solvent. Typically, this reaction is conducted at temperatures in the range of about from 50° to 110° C. using about from 5 to 0.5 moles of anhydride per mole of compound II.

The respective products of the above reactions can be isolated and purified by conventional techniques such as chromatography, distillation, crystallization, etc., when appropriate.

Definitions

The terms "oxyaminoalkylidene" and "oxyiminoalkyl" refer to the radical having the formula

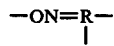

wherein R is alkyl. For example, the terms "1-allyloxyaminobutylidene" and "1-allyloxyiminobutyl" refer to the radical having the formula

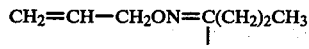

The products in the following Examples and Table A were identified by infrared and nmr spectroscopy and elemental analysis.

EXAMPLE 1

Preparation of 2-[1-(3-chloroallyloxyamino)butylidene]-5,5-dimethyl-cyclohexane-1,3-dione A. Dimedone (5,5-dimethylcyclohexane-1,3-dione, 99%, 14.2 g), pyridine (9 ml) and methylene chloride (100 ml) were mixed in a flask and butyryl chloride (11.4 g) was added dropwise. The mixture was stirred for 26 hours at room temperature and filtered. The filtrate was washed with HCl (6 N, 100 ml), water (100 ml), saturated $Na_2CO_3$ (50 ml), water (50 ml), dried ($MgSO_4$). The solvent was removed under reduced pressure to yield 3-butyroxy-5,5-dimethylcyclohex-2-en-1-one as a yellow liquid.

B. To a dry flask containing methylene chloride (30 ml) and aluminum chloride (26.67 g) at ice bath temperature was added dropwise a solution of the product of step A (21.03 g) in dichloromethane (50 ml). The mixture was stirred for 2½ hours then poured into 100 ml cold 6 N HCl slowly with stirring. The mixture stood overnight. The organic phase was collected and washed with saturated $Na_2CO_3$ (100 ml) and water (100 ml). The solvent was stripped to yield 15.9 g yellow liquid. The $Na_2CO_3$ wash was acidified to pH2 with concentrated HCl, extracted with $CH_2Cl_2$ and stripped to yield 4.8 g yellow liquid, identical to the composition of the 15.9 g of product. The combined products yielded 20.7 g 2-butyro-5,5-dimethylcyclohexane-1,3-dione.

C. To a solution of N-hydroxyphthalimide (33.6 g) in dimethylsulfoxide (200 ml) was added anhydrous potassium carbonate (28 g). After 10 minutes, 1,3-dichloropropene (20 ml) was added and the mixture was stirred at room temperature overnight. The mixture was poured into 1.2 liter ice-water and the resultant white precipitate was collected, washed with cold water (2×100 ml), airdried and crystallized from 1.1 liter ethyl alcohol. Yield: 41.0 g. N-(3-chloroallyloxy)-phthalimide, white needles.

D. The product from step C (21.2 g), absolute ethanol (650 ml) and hydrazine (3.7 g) were stirred in a flask and gradually heated to reflux. After 2 hours the mixture was cooled to room temperature, added to concentrated HCl (12.5 ml), then cooled to 0°. The precipitate was collected and washed with cold ethanol and water. The washings were concentrated to yield 21.5 of the crude product. This product was slurried with 50 ml methanol and the white solid was filtered and dried to yield 3.3 g of the crystalline product. The combined washings and filtrates were concentrated, and recrystallized (50 ml acetonitrile, 50 ml ether) to yield an additional 5.5 g of white crystalline product, 3-chloroallyloxyamine hydrochloride.

E. To a solution of sodium methoxide (460 mg) in methanol (10 ml) was added the product of step D (1.22 g) and the suspension was stirred at room temperature for 15 minutes. To this suspension was added a solution of 2-butyro-5,5-dimethyl-cyclohexane-1,3-dione (see step B above) in 10 ml methanol. After stirring for two days at room temperature, the solution was concentrated in vacuo. The residue was taken up in 30 ml ethyl acetate and 25 ml 10% NaOH, whereupon three layers formed. The bottom two layers were collected, cooled, acidified with con. HCl (pH 1) and extracted twice with 30 ml methylene chloride. The methylene chloride extracts were combined, washed with water (2×20 ml), dried ($MgSO_4$) and concentrated in vacuo to yield the liquid product, 2-[1-(3'-chloroallyloxyamino)-butylidene]-5,5-dimethylcyclohexane-1,3-dione. See compound No. 3 in Table A.

EXAMPLE 2

Preparation of 2-[1-(3'-chloroallyloxyamino)-propylidene]-5,5-dimethylcyclohexane-1,3-dione A. According to the procedure of Example 1A, 5,5-dimethylcyclohexane-1,3-dione (14.2 g) and propionyl chloride (9.7 g) were reacted in pyridine (9 ml) and methylene chloride (100 ml) to yield 21.0 g. 3-propionoxy-5,5-dimethylcyclohex-2-en-1-one.

B. The product of Example 2A (19.62 g) and aluminum chloride (26.67 g) were treated according to the procedure of Example 1B to yield 17.9 g. 2-propiono-5,5-dimethyl-cyclohexane-1,3-dione.

C. The product made according to Example 1D (1.22 g) and the product from Example 2B (1.65 g) were treated according to the procedure of Example 1E to yield the liquid product, 2-[1-(3'-chloroallyloxyamino)-propylidene]-5,5-dimethylcyclohexane-1,3-dione. See Compound No. 2 in Table A.

EXAMPLE 3

Trans-2-[1-(3-chloroallyloxyimino)butyl]-5-(2-ethylthiopropyl)cyclohexane-1,3-dione (a) 86.6 g of crotonaldehyde was added dropwise to a mixture containing 64.0 g of ethanethiol and 2 ml of triethylamine in 500 ml of acetonitrile at room temperature (about 20°-25° C.). The resulting mixture was stirred overnight (about 15 hours) at room temperature and then rotary evaporated to remove acetonitrile. The residue was dissolved in 300 ml of ethyl ether, washed twice with water, dried over magnesium sulfate and then concentrated by evaporation affording a yellow liquid concentrate of beta-ethylthiobutyraldehyde.

(b) A mixture containing 15.9 g of beta-ethylthiobutyraldehyde and 38.2 g of triphenylphosphoranylidene-2-propanone in 300 ml of methylene chloride was refluxed overnight and then evaporated affording a thick residue. The residue was mixed with hexane and filtered. The filtrate was evaporated under vacuum and the residue then distilled under vacuum affording 6-ethylthio-3-hepten-2-one.

(c) 2.53 g of metallic sodium were added to 100 ml of ethanol at room temperature. To this was then added 17.6 g of diethyl malonate, with stirring, and then 17.2 g of 6-ethylthio-3-hepten-2-one was added. The resulting mixture was then refluxed for four hours and then an aqueous sodium hydroxide solution, containing 9.5 g of sodium hydroxide in 75 ml of water, was added and the mixture refluxed for another two hours. The mixture was cooled to 50° C. and then acidified by the addition of concentrated hydrochloric acid. The mixture was then warm until decarboxylation was complete and then evaporated to a liquid residue. The residue was mixed with ethyl ether, washed with water, and evaporated to a brown liquid. The liquid was base, acid extracted affording 5-(2-ethylthiopropyl) cyclohexane-1,3-dione.

(d) 0.2 g of metallic sodium was dissolved in 1 ml of methanol and then added to 3.2 g of 5-(2-ethylthiopropyl)cyclohexane-1,3dione. 20 ml of butyric anhydride was added and the mixture then refluxed for three hours. The mixture was then evaporated and the residue mixed with methylene chloride and then extracted with aqueous 5 wt.% sodium hydroxide. The base extract was washed with methylene chloride, then acidified with concentrated hydrochloric acid and then extracted into methylene chloride. This was then evaporated affording 2-butyryl-5-(2-ethylthiopropyl) cyclohexane-1,3-dione.

(e) 0.38 g of sodium methoxide, 10 ml of methanol, and 1.0 g of 3-chloroallyloxyamine hydrochloride (H$_2$NOCH$_2$CH=CHCl) were admixed together and then stirred for 10 minutes at room temperature. 2 g of 2-butyryl-5-(2-ethylthiopropyl)cyclohexane-1,3-dione was added and the resulting mixture stirred for about two days at room temperature. The mixture was then concentrated by evaporation and the concentrate mixed with 60 ml of diethyl ether and 40 ml of water. The ether layer was extracted with 40 ml of aqueous 2 wt. % sodium hydroxide solution, washed with 20 ml of water, dried over anhydrous magnesium sulfate and evaporated affording a minor amount of the title compound as the trans isomer.

The 2% sodium hydroxide solution extract was acidified to about pH 1 with aqueous 6 N hydrochloric acid and then extracted with 100 ml of methylene chloride. The organic layer was washed with 40 ml of water, dried over magnesium sulfate and then evaporated affording the trans isomer of the title compound as the residue (Compound No. 54 of Table A hereinbelow). The major portion of the title compound was recovered from the sodium hydroxide extract.

EXAMPLE 4

This example illustrates the preparation of the acyloxy compounds of the invention.

To a reaction mixture containing 3.0 g (0.01) mol of 2-[1-(3'-chloroallyloxyamino)-butylidene]-5,5-dimethylcyclohexane-1,3-dione and 0.87 gm (0.011 mol) of pyridine in 20 ml of methylene chloride stirred at 0° C. is added 0.89 gm (0.011 mol) of acetyl chloride. The mixture is then stirred at room temperature for 2 hours. The mixture is then worked up by washing with water, drying with anhydrous magnesium sulfate, and filtered. The filtrate is evaporated under vacuum affording 3-acetyloxy-2-[1-(3'-chloroallyloxyamino)-butylidene]-5,5-dimethylcyclohex-2-en-1-one.

Similarly, by following the same procedure, the corresponding 3-acetyloxy derivative of each of the products listed in Table A hereinbelow are respectively prepared.

EXAMPLE 5

This example illustrates the preparation of the salts of the present invention.

To 3.0 gm (0.01 mol) of 2-[1-(3'-chloroallyloxyamino)-butylidene]-5,5-dimethylcyclohexane-1,3-dione in 10 ml of acetone is added 0.4 gm (0.01 mol) of sodium hydroxide dissolved in 2 ml of water. The solvents are evaporated under vacuum affording the 3-hydroxy sodium salt of 2-[1-(3'-chloroallyloxyamino)-butylidene]-3-hydroxy-5,5-dimethylcyclohex-2-en-1-one.

Similarly, by following the same procedure, the sodium salts of each of the products listed in Table A hereinbelow are respectively prepared.

UTILITY

The compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are especially effective against grassy weeds and by proper dosage regulation can be safely applied for the control or prevention of grasses in broad leaf crops. Moreover, certain of the compounds (for example 2-[1-(3-chloroallyloxyimino)-butyl]-5-(2-ethylthiopropyl)cyclohexane-1,3-dione and its 4-chlorobenzyl analog)exhibit excellent soil stability which is particularly advantageous for pre-emergence appication.

The compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert an herbicidal or growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered herbicidal compositions can be used. The active ingredient usually makes up from 0.5–90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benzene, toluene, and the like. The active ingredient usually makes up about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

When used as a pre-emergent treatment, it is desirable to include a fertilizer, an insecticide, a fungicide or another herbicide.

The amount of active compound or composition administered will vary with the particular plant part or plant growth medium which is to be contacted, the general location of application—i.e., sheltered areas such as greenhouses, as compared to exposed areas such as fields—as well as the desired type of control. Generally for both pre- and post-emergent herbicidal control, the compounds of the invention are applied at rates of 0.2 to 60 kg/ha, and the preferred rate is in the range of 0.5 to 40 kg/ha. For plant growth regulating or retarding activity, it is essential to apply the compounds at a concentration not so high as to kill the plants. Therefore, the application rates for plant growth regulating or retarding activity will generally be lower than the rate used for killing the plants. Generally, such rates vary from 0.1 to 5 kg/ha, and preferably from 0.1 to 3 kg/ha.

Herbicidal tests on representative compounds of the invention were made using the following methods.

Pre-Emergent Herbicidal Test

An acetone solution of the test compound was prepared by mixing 500 mg of the compound, 158 mg of a nonionic surfactant and 20 ml of acetone. Twenty ml of this solution was added to 80 ml of water to give the test solution.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table I.

In follow-up tests, the procedure above was repeated using diluted test solution which was sprayed onto the soil surface at various dosages. The results of these tests appear in Table II.

Post-Emergent Herbicidal Test

The test compound was formulated in the same manner as described above for the pre-emergent test. This formulation was uniformly sprayed on 2 similar pots of 24-day-old plants (approximately 15 to 25 plants per pot) at a dose of 27.5 micrograms/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table I.

In follow-up tests, the procedure above was repeated using diluted test solution which was sprayed onto the soil surface at various dosages. The results of these tests appear in Table II.

TABLE A

Compounds of the Formula

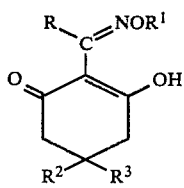

$R^2$ and $R^3$ are each methyl unless otherwise indicated

| No. | R | $R^1$ | mp °C. | C Calc. | C Fd. | H Calc. | H Fd. | N Calc. | N Fd. |
|---|---|---|---|---|---|---|---|---|---|
| 1 | $C_2H_5$ | $CH_2CCl=CH_2$ | Oil | 58.84 | 59.33 | 7.05 | 7.43 | 4.90 | 5.06 |
| 2 | $CH_3CH_2CH_2$ | $CH_2CCl=CH_2$ | Oil | 60.09 | 59.41 | 7.40 | 7.61 | 4.67 | 4.70 |
| 3 | $CH_3CH_2CH_2$ | Trans-$CH_2CH=CHCl$ | Oil | 60.09 | 62.13 | 7.40 | 7.80 | 4.67 | 4.88 |
| 4 | $C_2H_5$ | Trans-$CH_2CH=CHCl$ | Oil | 58.84 | 58.69 | 7.05 | 7.22 | 4.90 | 5.06 |
| 5 | $CH_3CH_2CH_2$ | $CH_2$-(2-Cl-phenyl) | Oil | 65.23 | 66.29 | 6.91 | 7.36 | 4.00 | 4.05 |
| 6 | $C_2H_5$ | $CH_2$-(2-Cl-phenyl) | Oil | 64.37 | 64.56 | 6.6 | 6.81 | 4.17 | 4.17 |
| 7 | $CH_3CH_2CH_2$ | $CH_2$-(4-Cl-phenyl) | Oil | 65.23 | 65.16 | 6.91 | 7.18 | 4.00 | 3.61 |
| 8 | $C_2H_5$ | $CH_2$-(4-Cl-phenyl) | Oil | 64.37 | 63.93 | 6.60 | 6.74 | 4.17 | 3.81 |
| 9 | $CH_3CH_2CH_2$ | $CH_2$-(4-F-phenyl) | Oil | 68.45 | 71.78 | 7.26 | 7.88 | 4.20 | 4.67 |
| 10 | $C_2H_5$ | $CH_2$-(3-F-phenyl) | Oil | 67.69 | 68.19 | 6.98 | 7.70 | 4.39 | 4.60 |
| 11 | $CH_3CH_2CH_2$ | $CH_2$-(4-F-phenyl) | Oil | 68.45 | 68.83 | 7.26 | 7.92 | 4.20 | 4.25 |
| 12 | $C_2H_5$ | $CH_2$-(4-F-phenyl) | Oil | 67.69 | 67.88 | 6.98 | 7.26 | 4.39 | 4.41 |
| 13 | $CH_3CH_2CH_2$ | $CH_2$-(3-Cl-phenyl) | Oil | 65.23 | 66.84 | 6.91 | 7.4 | 4.00 | 4.34 |

TABLE A-continued

Compounds of the Formula

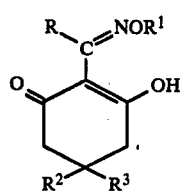

$R^2$ and $R^3$ are each methyl unless otherwise indicated

| No. | R | $R^1$ | mp °C. | C Calc. | C Fd. | H Calc. | H Fd. | N Calc. | N Fd. |
|---|---|---|---|---|---|---|---|---|---|
| 14 | $C_2H_5$ | CH$_2$-(3-Cl-C$_6$H$_4$) | Oil | 64.37 | 65.45 | 6.60 | 6.99 | 4.17 | 4.33 |
| 15 | $CH_3CH_2CH_2$ | CH$_2$-(2,6-Cl$_2$-C$_6$H$_3$) | 70–71 | 59.38 | 60.34 | 6.03 | 6.36 | 3.65 | 3.83 |
| 16 | $CH_3CH_2CH_2$ | (cis)-$CH_2CH=CHCl$ | Oil | 60.09 | 62.05 | 7.40 | 8.31 | 4.67 | 4.9 |
| 17 | $CH_3$ ($R^2 = H$, $R^3 = H$) | CH$_2$-(2-Cl-C$_6$H$_4$) | Oil | 61.33 | 61.45 | 5.49 | 6.43 | 4.43 | 4.56 |
| 18 | $CH_3$ ($R^2 = H$, $R^3 = H$) | CH$_2$-(2,6-Cl$_2$-C$_6$H$_3$) | 84.7 | 54.89 | 55.55 | 4.61 | 5.07 | 4.27 | 4.17 |
| 19 | $CH_3(CH_2)_3$ | $CH_2CCl=CH_2$ | Oil | 61.23 | 61.25 | 7.71 | 8.36 | 4.46 | 4.16 |
| 20 | $CH_3$ | $CH_2CCl=CH_2$ | Oil | 57.76 | 57.11 | 6.68 | 6.96 | 5.15 | 4.98 |
| 21 | $CH_3CH_2CH_2$ | $CH_2CCl=CHCl$ | Oil | 53.90 | 54.52 | 6.33 | 6.8 | 4.19 | 4.20 |
| 22 | $CH_3$ | $CH_2CCl=CHCl$ | Oil | 50.99 | 50.77 | 5.60 | 6.02 | 4.57 | 4.6 |
| 23 | $CH_3(CH_2)_3$ | $CH_2CCl=CHCl$ | Oil | 55.18 | 54.16 | 6.66 | 7.06 | 4.02 | 3.99 |
| 24 | $C_2H_5$ | $CH_2CCl=CHCl$ | Oil | 52.51 | 52.58 | 5.98 | 4.97 | 4.37 | 4.37 |
| 25 | $CH_3(CH_2)_3$ | CH$_2$-(4-F-C$_6$H$_4$) | Oil | 69.15 | 69.23 | 7.54 | 7.93 | 4.03 | 4.15 |
| 26 | $(CH_3)_2CHCH_2$ | CH$_2$-(4-F-C$_6$H$_4$) | Oil | 69.15 | 69.43 | 7.54 | 7.89 | 4.03 | 4.04 |
| 27 | $CH_3$ | (cis)-$CH_2CH=CHCl$ | Oil | 57.46 | 62.13 | 6.68 | 7.48 | 5.15 | 5.56 |
| 28 | $C_2H_5$ | (cis)-$CH_2CH=CHCl$ | Oil | 58.84 | 56.29 | 7.05 | 6.93 | 4.90 | 4.71 |
| 29 | $(CH_3)_2CHCH_2$ | (cis)-$CH_2CH=CHCl$ | Oil | 61.23 | 59.71 | 7.71 | 7.95 | 4.46 | 4.11 |
| 30 | $C_2H_5$ | CH$_2$-(2,4-Cl$_2$-C$_6$H$_3$) | Oil | 58.39 | 55.23 | 5.72 | 5.93 | 3.78 | 3.35 |

TABLE A-continued

Compounds of the Formula

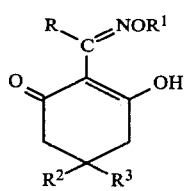

$R^2$ and $R^3$ are each methyl unless otherwise indicated

| No. | R | $R^1$ | mp °C. | C Calc. | C Fd. | H Calc. | H Fd. | N Calc. | N Fd. |
|---|---|---|---|---|---|---|---|---|---|
| 31 | $CH_3CH_2CH_2$ | CH₂—(2,3-diCl-phenyl) | Oil | 59.40 | 56.53 | 6.03 | 6.23 | 3.64 | 3.22 |
| 32 | $CH_3(CH_2)_3$ | CH₂—(2,3-diCl-phenyl) | Oil | 60.30 | 58.37 | 6.33 | 6.37 | 3.52 | 3.24 |
| 33 | $(CH_3)_2CHCH_2$ | CH₂—(2,3-diCl-phenyl) | Oil | 60.30 | 57.62 | 6.33 | 6.37 | 3.52 | 3.12 |
| 34* | $CH_3CH_2CH_2$ | $CH_2CCl=CH_2$ | Oil | 57.06 | 54.85 | 6.76 | 6.83 | 3.91 | 4.66 |
| 35 | $CH_3CH_2CH_2$ | $CH_2CH=CClCH_3$ | Oil | 61.23 | 62.67 | 7.71 | 7.90 | 4.46 | 5.12 |
| 36 | $CH_3$ | $CH_2$—(4-Cl-phenyl) | Oil | 63.45 | 61.30 | 6.26 | 6.14 | 4.35 | 3.98 |
| 37 | $CH_3$ | (trans)-$CH_2CH=CHCl$ | Oil | 57.46 | 59.93 | 6.78 | 7.01 | 5.02 | 5.57 |
| 38 | $CH_3$ | $CH_2CH=CClCH_3$ | Oil | 58.84 | 57.69 | 7.05 | 7.55 | 4.90 | 5.57 |
| 39 | $CH_3$ | $CH_2$—(4-F-phenyl) | 41–42 | 66.87 | 67.56 | 6.60 | 6.85 | 4.59 | 4.61 |
| 40 | $CH_3(CH_2)_3$ | $CH_2CH_2Cl$ | Oil | 59.69 | 61.65 | 8.02 | 8.46 | 4.64 | 4.04 |
| 41 | $CH_3CH_2CH_2$ | (cis)-$CH_2CH=CHCl$ | Oil | 57.06 | 57.38 | 6.76 | 7.05 | 3.91 | 4.76 |
| 42 | $C_2H_5$ | $CH_2$—(2,6-diCl-phenyl) | 70–71 | 58.39 | 58.71 | 5.72 | 5.89 | 3.78 | 3.97 |
| 43 | $CH_3CH_2CH_2$ | (cis)-$CH_2CH=CHCH_2Cl$ | Oil | 61.24 | 62.1 | 7.70 | 8.01 | 4.46 | 4.08 |
| 44 | $CH_3$ | $CH_2CH_2Cl$ | Oil | 55.49 | 55.88 | 6.98 | 7.02 | 5.39 | 4.18 |
| 45 | $C_2H_5$ | $CH_2CH=CClCH_3$ | Oil | 60.10 | 59.96 | 7.40 | 7.57 | 4.67 | 4.67 |
| 46 | $C_2H_5$ | (trans)-$CH_2CH=CHCH_2Cl$ | Oil | 60.10 | 60.21 | 7.40 | 7.71 | 4.67 | 3.74 |
| 47 | $CH_3CH_2CH_2$ | $CH_2CH_2O$—phenyl | Oil | 69.54 | 70.26 | 7.88 | 7.98 | 4.05 | 4.47 |

TABLE A-continued

Compounds of the Formula

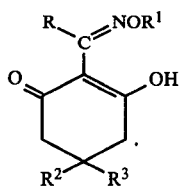

$R^2$ and $R^3$ are each methyl unless otherwise indicated

| No. | R | $R^1$ | mp °C. | C Calc. | C Fd. | H Calc. | H Fd. | N Calc. | N Fd. |
|---|---|---|---|---|---|---|---|---|---|
| 48 | $CH_3CH_2CH_2$ | $CH_2CH_2CH_2O$—phenyl | Oil | 70.17 | 68.52 | 8.13 | 8.36 | 3.90 | 3.48 |
| 49* | $C_2H_5$ | $CH_2$—(4-F-phenyl) | 54–60 | 66.47 | 67.43 | 6.69 | 7.26 | 3.88 | 4.08 |
| 50 | $C_2H_5$ | $CH_2$—(3-$CF_3$-phenyl) | Oil | 61.78 | 62.55 | 6.00 | 6.17 | 3.79 | 3.93 |
| 51 | $CH_3CH_2CH_2$ | $CH_2$—(3-$CF_3$-phenyl) | Oil | 62.35 | 63.3 | 6.31 | 6.63 | 3.65 | 3.76 |
| 52 | $C_2H_5$ | $CH_2$—(2,4-di-Cl-phenyl) | Oil | 58.39 | 57.10 | 5.72 | 5.50 | 3.78 | 3.84 |
| 53 | $CH_3CH_2CH_2$ | $CH_2$—(2,4-di-Cl-phenyl) | Oil | 59.38 | 56.02 | 6.03 | 5.58 | 3.64 | 3.78 |
| 54 | $CH_3CH_2CH_2$ | $CH_2CH\!=\!CHCl$(trans) | Oil | 57.82 | 57.03 | 7.55 | 7.42 | 3.76 | 3.72 |
| | ($R^2 = H$, $R^3 = -CH_2\underset{\underset{CH_3}{\mid}}{C}HSCH_2CH_3$) | | | | | | | | |
| 55 | $CH_3CH_2CH_2$ | $CH_2$—(4-Cl-phenyl) | Oil | 62.32 | 61.54 | 7.13 | 7.14 | 3.30 | 2.93 |
| | ($R^2 = H$, $R^3 = -CH_2\underset{\underset{CH_3}{\mid}}{C}HSCH_2CH_3$) | | | | | | | | |
| 56 | $C_2H_5$ | $CH_2$—(4-$NO_2$-phenyl) | Oil | 62.42 | 61.82 | 6.40 | 6.60 | 8.09 | 8.04 |
| A | $CH_3CH_2CH_2$ | $CH_2CH\!=\!CH_2$ | (See Patent No. 4,011,256) | | | | | | |

TABLE A-continued

Compounds of the Formula

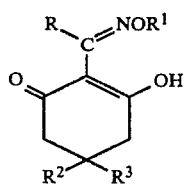

$R^2$ and $R^3$ are each methyl unless otherwise indicated

| No. | R | $R^1$ | mp °C. | C Calc. | C Fd. | H Calc. | H Fd. | N Calc. | N Fd. |
|---|---|---|---|---|---|---|---|---|---|
| 57 | $CH_3CH_2$ | $CH_2$—⟨C$_6$H$_4$⟩—$CF_3$ | Oil | 61.78 | 60.9 | 6.00 | 6.5 | 3.79 | 3.87 |
| 58 | $CH_3CH_2CH_2$ | $CH_2$—⟨C$_6$H$_4$⟩—$CF_3$ | Oil | 62.65 | 61.63 | 6.31 | 7.00 | 3.65 | 4.16 |

*Compound has —$CO_2CH_3$ substituent at the 4-position of cyclohexene ring

TABLE I

HERBICIDAL ACTIVITY
Pre/Post % Control (27.5 gamma/cm$^2$)

| No. | L | M | P | C | W | O |
|---|---|---|---|---|---|---|
| 1 | 0/0 | 0/0 | 0/0 | 100/75 | 100/100 | 50/93 |
| 2 | 0/50 | 20/55 | 30/35 | 100/60 | 100/98 | 90/68 |
| 3 | 30/25 | 10/20 | 35/20 | 100/100 | 100/100 | 100/100 |
| 4 | 40/10 | 23/25 | 35/0 | 100/100 | 100/100 | 100/100 |
| 5 | 0/35 | 40/55 | 45/45 | 98/50 | 100/68 | 55/15 |
| 6 | 40/40 | 60/58 | 43/63 | 65/25 | 80/40 | 30/0 |
| 7 | 0/45 | 0/55 | 0/28 | 100/70 | 100/100 | 100/100 |
| 8 | 0/25 | 0/65 | 0/40 | 100/75 | 100/100 | 85/100 |
| 9 | 0/55 | 0/65 | 0/50 | 100/20 | 100/88 | 55/30 |
| 10 | 0/45 | 0/45 | 0/30 | 98/35 | 100/83 | 48/23 |
| 11 | 20/40 | 0/35 | 0/23 | 100/53 | 100/100 | 100/100 |
| 12 | 15/23 | 0/30 | 0/13 | 100/60 | 100/100 | 68/20 |
| 13 | 0/23 | 0/73 | 0/0 | 98/35 | 98/90 | 75/88 |
| 14 | 0/13 | 0/60 | 0/0 | 95/33 | 100/88 | 65/78 |
| 15 | 0/0 | 0/0 | 0/0 | 95/40 | 100/95 | 65/53 |
| 16 | 0/40 | 0/60 | 0/20 | 100/90 | 100/100 | 73/100 |
| 17 | 0/45 | 0/30 | 0/0 | 0/0 | 0/0 | 0/0 |
| 18 | 0/25 | 10/35 | 10/23 | 0/0 | 0/0 | 0/0 |
| 19 | 0/55 | 0/68 | 0/30 | 45/23 | 93/58 | 35/10 |
| 20 | 30/0 | 0/0 | 0/0 | 65/70 | 98/100 | 35/20 |
| 21 | 0/55 | 0/88 | 0/28 | 100/45 | 100/98 | 60/88 |
| 22 | 20/23 | 0/60 | 0/23 | 55/25 | 100/98 | 35/0 |
| 23 | 0/38 | 0/98 | 0/28 | 55/10 | 100/70 | 30/10 |
| 24 | 30/35 | 0/75 | 0/23 | 100/28 | 100/95 | 55/38 |
| 25 | 25/40 | 0/88 | 0/30 | 45/20 | 33/0 | 33/0 |
| 26 | 0/30 | 0/55 | 0/0 | 85/20 | 95/80 | 53/100 |
| 27 | 0/0 | 0/0 | 0/0 | 98/65 | 100/100 | 40/80 |
| 28 | 20/28 | 10/— | 0/0 | 100/60 | 100/100 | 53/100 |
| 29 | 0/28 | 0/70 | 0/0 | 70/0 | 100/98 | 50/45 |
| 30 | 0/50 | 0/40 | 0/48 | 63/23 | 100/80 | 35/20 |
| 31 | 0/28 | 0/38 | 0/0 | 45/20 | 100/45 | 55/55 |
| 32 | 0/35 | 0/60 | 0/0 | 0/0 | 0/25 | 0/0 |
| 33 | 0/43 | 0/23 | 0/40 | 0/0 | 25/15 | 15/0 |
| 34 | 0/25 | 0/0 | 0/0 | 80/30 | 100/100 | 53/98 |
| 35 | 48/33 | 0/63 | 0/0 | 95/23 | 100/93 | 43/75 |
| 36 | 35/20 | 0/0 | 25/0 | 98/55 | 100/100 | 48/90 |
| 37 | 50/35 | 0/55 | 0/0 | 100/90 | 100/100 | 53/98 |
| 38 | 0/15 | 0/0 | 0/0 | 98/60 | 100/98 | 35/20 |
| 39 | 35/33 | 0/0 | 0/0 | 100/68 | 100/100 | 43/93 |
| 40 | 70/25 | 0/38 | 0/25 | 40/10 | 50/43 | 30/0 |
| 41 | 33/13 | 0/0 | 13/15 | 100/55 | 100/100 | 65/98 |
| 42 | 18/28 | 0/0 | 15/33 | 53/0 | 53/28 | 0/25 |
| 43 | 0/25 | 0/0 | 0/0 | 25/25 | 55/60 | 20/20 |
| 44 | 60/0 | 0/0 | 0/0 | 55/60 | 100/93 | 35/35 |
| 45 | 0/30 | 0/0 | 0/0 | 63/35 | 100/95 | 45/75 |
| 46 | 15/23 | 0/0 | 0/0 | 15/25 | 60/45 | 15/20 |
| 47 | 0/30 | 0/0 | 0/0 | 90/43 | 100/60 | 50/25 |
| 48 | 0/25 | 0/43 | 0/25 | 100/30 | 100/90 | 33/25 |
| 49 | 0/0 | 0/0 | 0/0 | 100/70 | 100/100 | 35/100 |
| 50 | 43/15 | 20/55 | 15/15 | 60/30 | 60/58 | 45/15 |
| 51 | 35/15 | 0/0 | 0/15 | 100/50 | 90/65 | 55/90 |
| 52 | 0/25 | 0/45 | 0/23 | 40/20 | 85/40 | 0/0 |
| 53 | 0/35 | 0/80 | 0/40 | 70/20 | 98/58 | 30/20 |
| 54 | 0/40 | 0/20 | 0/0 | 100/100 | 100/100 | 100/100 |
| 55 | 0/30 | 0/10 | 0/18 | 100/100 | 100/100 | 100/100 |
| 56 | 0/0 | 0/0 | 0/0 | 98/98 | 100/100 | 50/100 |
| 57 | 60/0 | 70/55 | 35/45 | —/90 | 100/95 | 78/88 |
| 58 | 0/25 | 0/55 | 0/45 | —/80 | 100/100 | 100/100 |

L = Lambsquarter (*Chenopodium album*)
M = Mustard (*Brassica arvensis*)
P = Pigweed (*Amaranthus retroflexus*)
C = Crabgrass (*Digitaria sanguinalis*)
W = Watergrass (*Echinochloa crusgalli*)
O = Wild Oats (*Avenua fatua*)

TABLE II

HERBICIDAL ACTIVITY
Pre/Post % Control (rate in gamma/cm$^2$)

| No. | Rate | Soybeans | Rice | L | M | P | C | W | O |
|---|---|---|---|---|---|---|---|---|---|
| 1 | 11 | 0/0 | 99/82 | 37/0 | 0/25 | 0/3 | 97/52 | 100/100 | 80/65 |
|   | 4.4 | 0/0 | 73/3 | 0/0 | 0/0 | 0/0 | 93/7 | 100/99 | 80/7 |
|   | 1.8 | 0/0 | 27/0 | 0/0 | 0/0 | 0/0 | 52/0 | 99/95 | 28/0 |
|   | 0.7 | 0/0 | 5/0 | 0/0 | 0/0 | 0/0 | 23/0 | 55/7 | 0/0 |
| 2 | 27.5 | —/25 | —/55 | —/50 | —/55 | —/35 | —/60 | —/98 | —/68 |
|   | 4.4 | 0/— | 95/— | 0/— | 0/— | 0/— | 23/— | 55/— | 0/— |
|   | 1.8 | 0/— | 83/— | 0/— | 0/— | 0/— | 88/— | 100/— | 77/— |

TABLE II-continued
HERBICIDAL ACTIVITY
Pre/Post % Control (rate in gamma/cm²)

| No. | Rate | Soybeans | Rice | L | M | P | C | W | O |
|---|---|---|---|---|---|---|---|---|---|
|  | 0.7 | 0/— | 60/— | 0/— | 0/— | 0/— | 83/— | 100/— | 58/— |
| 3 | 4.4 | 0/10 | 100/95 | 0/0 | 0/0 | 0/0 | 93/75 | 100/100 | 95/99 |
|  | 1.8 | 0/0 | 92/88 | 0/0 | 0/0 | 0/0 | 82/27 | 100/100 | 90/93 |
|  | 0.7 | 0/0 | 73/60 | 0/0 | 0/0 | 0/0 | 53/20 | 100/97 | 62/52 |
|  | 0.28 | 0/0 | 27/7 | 0/0 | 0/0 | 0/0 | 22/0 | 100/95 | 33/23 |
| 4 | 4.4 | 0/0 | 100/100 | 0/0 | 0/0 | 0/0 | 98/100 | 100/100 | 95/99 |
|  | 1.8 | 0/0 | 100/98 | 0/0 | 0/0 | 0/0 | 98/100 | 100/100 | 87/95 |
|  | 0.7 | 0/0 | 97/95 | 0/0 | 0/0 | 0/0 | 82/83 | 100/95 | 58/— |
|  | 0.28 | 0/0 | 80/50 | 0/0 | 0/0 | 0/0 | 67/12 | 100/90 | 0/0 |
| 5 | 27.5 | —/10 | —/10 | —/35 | —/55 | —/45 | —/50 | —/68 | —/15 |
|  | 4.4 | 0/— | 12/— | 0/— | 0/— | 0/— | 25/— | 78/— | 20/— |
|  | 1.8 | 0/— | 0/— | 0/— | 0/— | 0/— | 7/— | 58/— | 0/— |
|  | 0.7 | 0/— | 0/— | 0/— | 0/— | 0/— | 0/— | 0/— | 0/— |
|  | 0.28 | 0/— | 0/— | 0/— | 0/— | 0/— | 0/— | 0/— | 0/— |
| 6 | 27.5 | 20/20 | 48/13 | 40/40 | 60/58 | 43/63 | 65/25 | 80/40 | 30/0 |
| 7 | 4.4 | 0/1 | 100/96 | 0/0 | 0/0 | 0/0 | 77/0 | 100/100 | 90/100 |
|  | 1.8 | 0/3 | 92/60 | 0/0 | 0/0 | 0/0 | 57/0 | 100/98 | 78/97 |
|  | 0.7 | 0/0 | 90/0 | 0/0 | 0/0 | 0/0 | 8/0 | 85/92 | 67/85 |
|  | 0.28 | 0/0 | 30/0 | 0/0 | 0/0 | 0/0 | 0/0 | 25/40 | 15/7 |
| 8 | 4.4 | 0/4 | 100/96 | 20/0 | 0/0 | 0/0 | 87/7 | 100/98 | 95/76 |
|  | 1.8 | 0/0 | 83/57 | 0/0 | 0/0 | 0/0 | 13/0 | 87/95 | 7/32 |
|  | 0.7 | 0/0 | 18/12 | 0/0 | 0/0 | 0/0 | 0/0 | 22/73 | 0/0 |
|  | 0.28 | 0/0 | 0/0 | 0/0 | 0/0 | 0/0 | 0/0 | 7/0 | 0/0 |
| 11 | 4.4 | 2/0 | 97/72 | 0/0 | 0/0 | 0/0 | 57/0 | 100/100 | 48/100 |
|  | 1.8 | 0/0 | 40/30 | 0/0 | 0/0 | 0/0 | 0/0 | 63/95 | 15/68 |
|  | 0.7 | 0/0 | 0/0 | 0/0 | 0/0 | 0/0 | 0/0 | 20/73 | 0/7 |
|  | 0.28 | 0/— | 0/— | 0/0 | 0/0 | 0/0 | 0/— | 0/— | 0/— |
| 16 | 4.4 | 0/0 | 78/57 | 0/0 | 0/0 | 63/0 | 60/25 | 100/100 | 27/92 |
|  | 1.8 | 0/0 | 65/10 | 0/0 | 0/0 | 65/0 | 0/3 | 92/98 | 0/15 |
|  | 0.7 | 0/0 | 3/3 | 0/0 | 0/0 | 0/0 | 0/0 | 40/95 | 0/0 |
|  | 0.28 | 0/0 | 0/0 | 0/0 | 0/0 | 0/0 | 0/0 | 0/32 | 0/0 |
| 19 | 27.5 | 0/10 | 13/0 | 0/55 | 0/68 | 0/30 | 45/23 | 93/58 | 35/10 |
| 20 | 27.5 | 0/0 | 50/60 | 0/30 | 0/0 | 0/0 | 70/65 | 100/98 | 20/35 |
| 22 | 27.5 | 0/0 | 43/55 | 20/23 | 0/60 | 0/23 | 55/25 | 100/98 | 35/0 |
| 23 | 27.5 | 0/20 | 20/10 | 0/38 | 0/98 | 0/28 | 55/10 | 100/70 | 30/10 |
| 24 | 27.5 | 0/0 | 78/50 | 30/25 | 0/75 | 0/23 | 100/28 | 100/95 | 78/38 |
| 27 | 4.4 | 0/0 | 77/87 | 0/0 | 0/0 | 0/0 | —/93 | 100/100 | 13/17 |
|  | 1.8 | 0/0 | 53/10 | 0/0 | 0/0 | 0/0 | —23 | 43/93 | 0/0 |
|  | 0.7 | 0/0 | 0/0 | 0/0 | 0/0 | 0/0 | —/0 | 0/13 | 0/0 |
| 28 | 27.5 | —/0 | —/? | —/— | —/— | —/0 | —/— | —/— | —/— |
|  | 4.4 | 0/— | 72/— | 0/— | 0/— | 0/— | —/— | 100/— | 47/— |
|  | 1.8 | 0/— | 53/— | 0/— | 0/— | 0/— | —/— | 92/— | 0/— |
|  | 0.7 | 0/— | 10/— | 0/— | 0/— | 0/— | —/— | 63/— | 0/— |
|  | 0.28 | 0/— | 0/— | 0/— | 0/— | 0— | —/— | 0/— | 0/— |
| 29 | 27.5 | 0/0 | 60/20 | 0/28 | 0/70 | 0/0 | 70/0 | 100/98 | 50/45 |
| A | 4.4 | 0/0 | 90/90 | 0/0 | 0/0 | 0/0 | —/100 | 100/100 | 88/100 |
|  | 1.8 | 0/0 | 62/62 | 0/0 | 0/0 | 0/0 | —/100 | 98/100 | 52/63 |
|  | 0.7 | 0/0 | 37/37 | 0/0 | 0/0 | 0/0 | —/22 | 65/80 | 40/22 |
|  | 0.28 | 0/0 | 3/3 | 0/0 | 0/0 | 0/0 | —/0 | 0/10 | 7/0 |
| 37 | 4.4 | 0/10 | 100/100 | 0/0 | 0/0 | 0/0 | —/100 | 100/100 | 47/93 |
|  | 1.8 | 0/0 | 98/77 | 0/0 | 0/0 | 0/0 | —/85 | 100/98 | 45/15 |
|  | 0.7 | 0/0 | 35/12 | 0/0 | 0/0 | 0/0 | —/22 | 100/47 | 22/0 |
|  | 0.28 | 0/ | 2/0 | 0/0 | 0/0 | 0/0 | —/0 | 52/7 | 0/0 |
| 39 | 4.4 | 0/0 | 72/98 | 0/0 | 0/0 | 0/0 | —/77 | 100/100 | 42/73 |
|  | 1.8 | 0/0 | 62/73 | 0/0 | 0/0 | 0/0 | —/13 | 98/92 | 0/0 |
|  | 0.7 | 0/0 | 32/12 | 0/0 | 0/0 | 0/0 | —/0 | 55/75 | 0/0 |
|  | 0.28 | 0/0 | 0/0 | 0/0 | 0/0 | 0/0 | —/0 | 32/0 | 0/0 |
| 46 | 11 | —/5 | —/87 | —/0 | —/32 | —/25 | —/13 | —/100 | —/100 |
|  | 4.4 | 0/0 | 90/48 | 0/0 | 0/0 | 0/0 | 32/0 | 100/100 | 60/82 |
|  | 1.8 | 0/0 | 60/13 | 0/0 | 0/0 | 0/0 | 3/0 | 100/98 | 45/73 |
|  | 0.7 | 0/0 | 13/5 | 0/0 | 0/0. | 0/0 | 0/0 | 40/58 | 0/12 |
|  | 0.28 | 0/— | 8/— | 0/— | 0/— | 0/— | 0/— | 13/— | 0/— |
| 54 | 4.4 | 2/0 | 100/100 | 0/0 | 0/0 | 0/0 | 94/97 | 100/100 | 99/100 |
|  | 1.8 | 0/0 | 100/100 | 0/0 | 0/0 | 0/0 | 95/90 | 100/100 | 96/100 |
|  | 0.7 | 0/0 | 99/100 | 0/0 | 0/0 | 0/0 | 73/50 | 98/98 | 85/100 |
|  | 0.28 | 0/0 | 73/82 | 0/0 | 0/0 | 0/0 | 13/15 | 58/90 | 73/87 |
| 55 | 4.4 | 5/0 | 98/100 | 0/0 | 0/0 | 0/0 | 93/75 | 100/100 | 99/100 |
|  | 1.8 | 2/0 | 87/100 | 0/0 | 0/0 | 0/0 | 33/58 | 100/100 | 92/100 |
|  | 0.7 | 0/0 | 57/97 | 0/0 | 0/0 | 0/0 | 0/15 | 98/98 | 77/98 |
|  | 0.28 | 0/0 | 0/62 | 0/0 | 0/0 | 0/0 | 0/0 | 10/92 | 62/82 |

Obviously many modifications and variations of the invention, described hereinabove and below in the claims, can be made without departing from the essence and scope thereof.

What is claimed is:

1. A compound of the formula

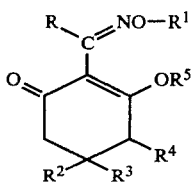

wherein

R is alkyl of 1 to 6 carbon atoms or phenyl;

$R^1$ is haloalkenyl of 2 to 6 carbon atoms and 1 to 3 halogen atoms, p-halobenzyl or p-trifluoromethylbenzyl;

$R^2$ and $R^3$ are independently hydrogen, alkyl of 1 to 3 carbon atoms, alkylthio of 1 to 6 carbon atoms, or alkylthioalkyl of 2 to 8 carbon atoms;

$R^4$ is hydrogen, or carbalkoxy of 2 to 4 carbon atoms;

$R^5$ is hydrogen, a cation, or

wherein $R^6$ is alkyl of 1 to 6 carbon atoms, phenyl or naphthyl.

2. The compound of claim 1 wherein $R^4$ and $R^5$ are each hydrogen.

3. The compound of claim 2 wherein R is alkyl of 1 to 6 carbon atoms.

4. The compound of claim 3 wherein $R^1$ is said haloalkenyl.

5. The compound according to claim 4 wherein $R^2$ and $R^3$ are alkyl of 1 to 3 carbon atoms.

6. The compound according to claim 5 wherein R is propyl, $R^2$ and $R^3$ are methyl and $R^1$ is 3-trans-chloroallyl.

7. The compound according to claim 5 wherein R is ethyl, $R^2$ and $R^3$ are methyl and $R^1$ is 3-trans-chloroallyl.

8. The compound of claim 1 wherein $R^1$ is p-halobenzyl or p-trifluoromethylbenzyl.

9. The compound of claim 8 wherein $R^2$ and $R^3$ are independently alkyl of 1 to 3 carbon atoms.

10. The compound of claim 9 wherein R is ethyl or propyl, $R^2$ and $R^3$ are each methyl, $R^4$ is hydrogen and $R^1$ is p-chlorobenzyl.

11. The compound of claim 9 wherein R is ethyl or propyl, $R^2$ and $R^3$ are each methyl, $R^4$ is hydrogen and $R^1$ is p-trifluoromethylbenzyl.

12. The compound of claim 1 wherein R is alkyl and one of $R^2$ or $R^3$ is hydrogen and the other is alkylthioalkyl.

13. The compound of claim 12 wherein $R^4$ is hydrogen.

14. The compound of claim 13 wherein $R^1$ is haloalkenyl or p-halobenzyl and R is ethyl or propyl.

15. The compound of claim 14 wherein $R^5$ is hydrogen and R is propyl.

16. The compound of claim 1 wherein R is ethyl or propyl and one of $R^2$ or $R^3$ is hydrogen and the other is 2-ethylthiopropyl.

17. The compound of claim 16 wherein R is propyl, $R^4$ is hydrogen and $R^1$ is haloalkenyl or p-halobenzyl.

18. The compound of claim 17 wherein $R^1$ is 3-trans-chloroallyl or 4-chlorobenzyl.

19. The compound of claim 18 wherein $R^1$ is 3-trans-chloroallyl and $R^5$ is hydrogen.

20. The compound of claim 18 wherein $R^1$ is 4-chlorobenzyl and $R^5$ is hydrogen.

21. A herbicidal composition comprising a biologically inert carrier and a herbicidally effective amount of a compound of the formula defined in claim 1.

22. A method of killing vegetation which comprises applying to said vegetation or its growth environment a herbicidally effective amount of a compound of the formula defined in claim 1.

23. A method of killing crabgrass, watergrass or wild oats which comprises applying thereto or its growth environment a herbicidally effective amount of a compound of the formula defined in claim 1.

24. A method of killing watergrass which comprises applying thereto or its growth environment a herbicidally effective amount of a compound of the formula defined in claim 1.

* * * * *